United States Patent
Khare

(10) Patent No.: US 9,507,914 B2
(45) Date of Patent: Nov. 29, 2016

(54) USER-DEFINABLE MORPHERS FOR MEDICAL DATA AND GRAPHICAL USER INTERFACE FOR THE SAME

(71) Applicant: Merge Healthcare Incorporated, Chicago, IL (US)

(72) Inventor: Amit Khare, Waukesha, WI (US)

(73) Assignee: Merge Healthcare Incorporated, Chicago, IL (US)

( * ) Notice: Subject to any disclaimer, the term of this patent is extended or adjusted under 35 U.S.C. 154(b) by 210 days.

(21) Appl. No.: 14/282,088

(22) Filed: May 20, 2014

(65) Prior Publication Data

US 2015/0022556 A1    Jan. 22, 2015

Related U.S. Application Data

(60) Provisional application No. 61/847,142, filed on Jul. 17, 2013.

(51) Int. Cl.
*G06F 19/00* (2011.01)

(52) U.S. Cl.
CPC .......... *G06F 19/345* (2013.01); *G06F 19/321* (2013.01); *G06F 19/3406* (2013.01)

(58) Field of Classification Search
None
See application file for complete search history.

(56) References Cited

U.S. PATENT DOCUMENTS

| | | | |
|---|---|---|---|
| 5,642,513 A * | 6/1997 | Schnellinger | H04L 45/00 717/117 |
| 5,999,179 A * | 12/1999 | Kekic | H04L 41/0213 715/734 |
| 8,069,420 B2 | 11/2011 | Plummer | |
| 8,280,483 B2 | 10/2012 | Zhu et al. | |
| 2002/0016719 A1 | 2/2002 | Nemeth et al. | |
| 2009/0228299 A1 | 9/2009 | Kangarloo et al. | |
| 2009/0287500 A1 | 11/2009 | Benjamin et al. | |
| 2014/0330855 A1 * | 11/2014 | Atanasiu | G06F 17/30389 707/759 |

FOREIGN PATENT DOCUMENTS

WO    2005101279    10/2005

OTHER PUBLICATIONS

NetBeans, "Debugging PHP Source Code in the NetBeans IDE," Jun. 6, 2012.*

(Continued)

*Primary Examiner* — Kee M Tung
*Assistant Examiner* — Nicholas R Wilson
(74) *Attorney, Agent, or Firm* — Michael Best & Friedrich LLP

(57) ABSTRACT

Systems, methods, and computer-readable medium containing instructions for processing image data. One system includes at least one processor configured to generate a graphical user interface ("GUI"). Through the GUI, the at least one processor receives a matching condition and a morphing action from a user. The morphing action includes an action to perform on a data attribute associated with image data when the image data satisfies the matching condition. Based on the received matching condition and morphing action, the at least one processor creates executable code. The at least one processor also receives image data including an image data attribute and executes the executable code to determine if the received image data satisfies the matching condition. If the image data satisfies the matching condition, the at least one processor automatically performs the morphing action on the received image data attribute.

20 Claims, 23 Drawing Sheets

(56) References Cited

OTHER PUBLICATIONS

Brink, "Windows 7 : Priority Level—Set for Applications and Processes," http://www.sevenforums.com/tutorials/83361-priority-level-set-applications-processes.html, May 7, 2010.*

Prohorenko et al., "Using Junit with Eclipse IDE," http://www.onjava.com/lpt/a/4524 2004.*

Lofstead, J. et al., "XChange: High Performance Data Morphing in Distributed Applications," College of Computing, Georgia Institute of Technology, 2005, 31 pages.

* cited by examiner

Match when ALL of the following are true (AND)
  Value of Patient ID(0010,0020) tag equals AM5001
  Age of Patient's Birth Date(0010,0030) tag greater than 50
  Match when ANY of the following are true (OR)
    DataElement of PatientBirthDate exists

USER-DEFINABLE MORPHERS FOR MEDICAL DATA AND GRAPHICAL USER INTERFACE FOR THE SAME

RELATED APPLICATION

The present application claims priority to U.S. Provisional Patent Application No. 61/847,142, filed on Jul. 17, 2013, the entire content of which is hereby incorporated by reference.

FIELD

Embodiments of the present invention relate to systems and methods for allowing users to define morphers for medical data, such as medical images.

BACKGROUND

In the field of medical imaging, vendors each have their own implementation of various standards, such as the Digital Imaging and Communications in Medicine ("DICOM") standard. Therefore, discrepancies can arise because different systems have different understandings, usages, and management of the DICOM standard (i.e., the DICOM attributes associated with medical imaging) and other such standards.

SUMMARY

Morphers can be used to fix the discrepancies referenced above. Morphers are small software modules that alter DICOM image attributes (e.g., a patient identifier, patient name, issuers of patient identifiers, etc.) and image attributes following other standards, using morphing actions when certain matching conditions are met. It should be noted that although the following description references the DICOM standard, the present invention is equally applicable to other types of imaging standards. Accordingly, the DICOM standard is referenced below only by way of example and for ease of description. In some embodiments, a morpher is used on a DICOM image received by an archive from a designated source (e.g., into a vendor neutral archive ("VNA"), output to another archive or DICOM-compliant entity, or based on other specific events, such as a query). Matching conditions are conditions that should be met before the associated morphing action or actions are executed on a dataset that alters DICOM image attributes. A matching condition can include whether an image attribute matches a particular value or falls within a range of values, whether an image attribute exists, etc. For example, an example matching condition may be the value of attribute "patient identifier" starts with the letter "A" or the value of attribute "image modality" is "CR." In some embodiments, a matching condition evaluates to a "TRUE" value or a "FALSE" value.

A morphing action is the corresponding action that is performed when matching conditions are met. For example, a morphing action can delete an image attribute, add an image attribute, or modify an image attribute (e.g., add a prefix "INT" to a patient name).

Morphers are currently programmed into archiving systems and typically have a high level of complexity. Therefore, new morphers usually have a long lead time because a programmer typically has to code a new morpher to handle every new or different customization.

Accordingly, embodiments of the present invention provide methods and systems for allowing users to define, edit, and simulate morphers. One embodiment of the invention provides a graphical user interface ("GUI") that allows users to define, edit, and simulate morphers. In some embodiments, the morphers are defined using a specialty programming language, and are processed by a morphing engine that includes a rules engine and a morphing core. The rules engine assembles the code for each user-defined morpher, and the morphing core initializes and executes a morpher.

In some embodiments, the invention provides a method of processing image data, and includes generating, by a processor, a graphical user interface for display to a user, receiving, by the processor, a matching condition from the user through the graphical user interface, and receiving, by the processor, a morphing action from the user through the graphical user interface. The morphing action can include an action to perform on a data attribute associated with image data when the image data satisfies the matching condition. The method can also include automatically creating, by the processor, executable code based on the morphing action and the matching condition. Furthermore, the method can include receiving image data including an image data attribute, automatically executing the executable code to determine if the received image data satisfies the matching condition, and, when the image data satisfies the matching condition, automatically performing the morphing action on the received image data attribute.

Some embodiments of the present invention provide a system for processing image data having at least one processor configured to generate a graphical user interface ("GUI"), wherein through the GUI, the at least one processor receives a matching condition and a morphing action from a user, and wherein the morphing action includes an action to perform on a data attribute associated with image data when the image data satisfies the matching condition. Based on the received matching condition and morphing action, the at least one processor can create executable code. The at least one processor can also receive image data including an image data attribute, and can execute the executable code to determine if the received image data satisfies the matching condition. If the image data satisfies the matching condition, the at least one processor can automatically perform the morphing action on the received image data attribute.

In some embodiments, the present invention provides non-transitory computer-readable medium that contains executable instructions for generating a graphical user interface for display to a user, receiving a matching condition from the user through the graphical user interface, receiving a morphing action from the user through the graphical user interface, and automatically creating executable code based on the morphing action and the matching condition. The morphing action can include an action to perform on a data attribute associated with image data when the image data satisfies the matching condition. The medium can further contain executable instructions for receiving image data including an image data attribute, automatically executing the executable code to determine if the received image data satisfies the matching condition, and, when the image data satisfies the matching condition, automatically performing the morphing action on the received image data attribute.

Other aspects of the invention will become apparent by consideration of the detailed description and accompanying drawings.

DETAILED DESCRIPTION

Figure 1:
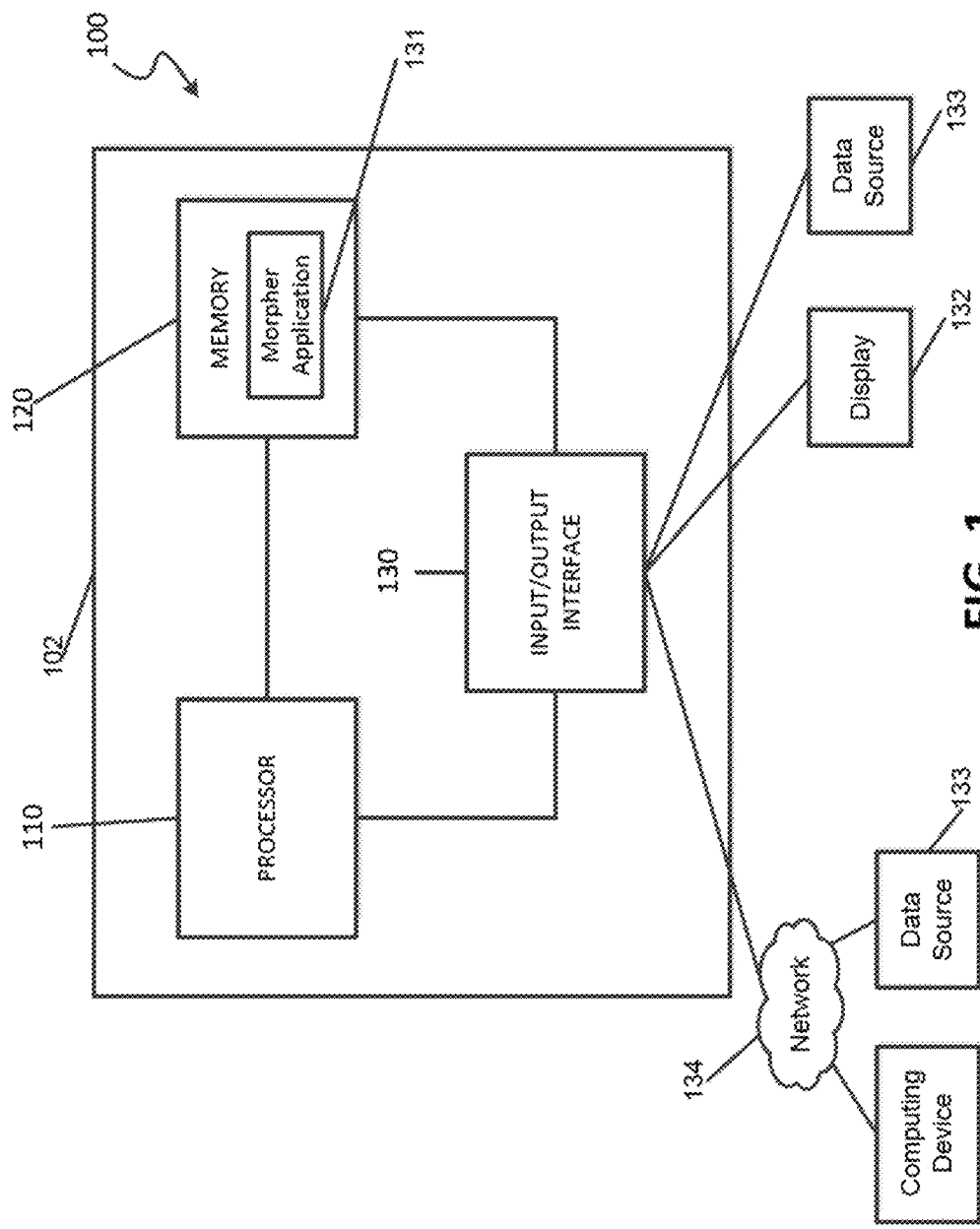
FIG. 1 schematically illustrates a system for processing image data.

Before embodiments of the present invention are explained in detail, it is to be understood that the invention is not limited in its application to the details of construction and the arrangement of components set forth in the following description or illustrated in the accompanying drawings. The invention is capable of other embodiments and of being practiced or of being carried out in various ways.

Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect. Also, electronic communications and notifications may be performed using any known means including direct connections, wireless connections, etc.

It should be noted that a plurality of hardware and software based devices, as well as a plurality of different structural components may be utilized to implement the invention. In particular, when terms such as controller, control unit, module, etc. are used in the following detailed description, it should be understood that these terms can represent non-transitory computer-readable medium encoded with instructions that when executed by a processing unit result in various actions and computations. Furthermore, and as described in subsequent paragraphs, the specific configurations illustrated in the drawings are intended to exemplify embodiments of the invention and that other alternative configurations are possible.

As noted above, embodiments of the invention provide methods and systems for allowing a user to define and manage morphers (e.g., creating, editing, deleting, simulating, etc.). FIG. 1 schematically illustrates a system 100 according to an embodiment of the invention. The system 100 includes a computing device 102. The computing device 102 can include a desktop computer, a laptop computer, a tablet computer, a smartphone, or another device configured to execute instructions and provide output. As illustrated in FIG. 1, the computing device 102 includes a processor 110, a memory module 120 including computer-readable medium, and an input/output interface 130. The processor 110, memory module 120, and input/output interface 130 are connected by one or more connections, such as a system bus. It should be understood that although only one processor 110, memory module 120, and input/output interface 130 are illustrated in FIG. 1, the computing device 102 can include multiple processors 110, memory modules 120, and/or input/output interfaces 130.

The processor 110 retrieves and executes instructions stored in the memory module 120. The processor 110 can also store data to the memory module 120. The memory module 120 can include a non-transitory computer readable medium and can include volatile memory, non-volatile memory, or a combination thereof. As illustrated in FIG. 1, the memory module 120 can store a morpher application 131. As described below in more detail, the morpher application 131, when executed by the processor 110, allows a user to define, edit, and configure morphers (i.e., executable code that automatically performs a predetermined morphing action on data that satisfies a predetermined matching condition). In particular, the application 131 can generate a graphical user interface ("GUI") that allows a user (who may have little or no programming experience) to design a morpher. It should be understood that the morpher application 131 can be distributed among multiple applications or modules. For example, in some embodiments, the morpher application 131 includes a rules engine and a morpher core. As described in more detail below, the rules engine can be configured to create morphers, whereas the morpher core initializes and executes morphers. In some embodiments, the memory 120 also stores morphers created through the application 131 and/or through other means.

The input/output interface 130 can exchange information with one or more external devices or systems. For example, the computing device 102 can communicate with one or more peripheral devices 132, such as a monitor or screen, a keyboard, a mouse, a printer, etc., through the input/output interface 130. For example, as noted above, the processor 110 can execute the application 131 to generate a GUI that is transmitted to and displayed by a monitor or screen. It should be understood that in some embodiments the monitor is included in the computing device 102 rather than as an external, peripheral device.

The computing device 102 can also communicate with one or more data sources 133 through the input/output interface 130. For example, the data source 133 can include a database that stores medical image data, and the computing device 102 can receive image data from the data source and/or transmit image data to the data source 133 for storage. In some embodiments, the data source 133 can also include an imaging modality or other device that generates or provides image data.

As illustrated in FIG. 1, in some embodiments, the computing device 102 also communicates with one more external devices over at least one network 134 (e.g., via a TCP/IP, LAN or WAN connection) through the input/output interface 130. For example, the computing device 102 can communicate with a data source 133 over the network 134. Alternatively or in addition, the computing device 102 can communicate with other computing devices over a network. For example, in some embodiments, the computing device 102 stores the morpher application 131 and a user directly interacts with the computing device 102 to use and interface with the morpher application 131. In other embodiments, the computing device 102 stores the morpher application 131 but hosts the morpher application 131 as a server accessible by a user indirectly through the use of another computing device (e.g., through a browser-application executed by the user's computing device). Furthermore, in some embodiments, the computing device 102 may interact directly with a user but may request data from other computing devices, such as other servers (e.g., storing information regarding existing morphers).

Figure 2:
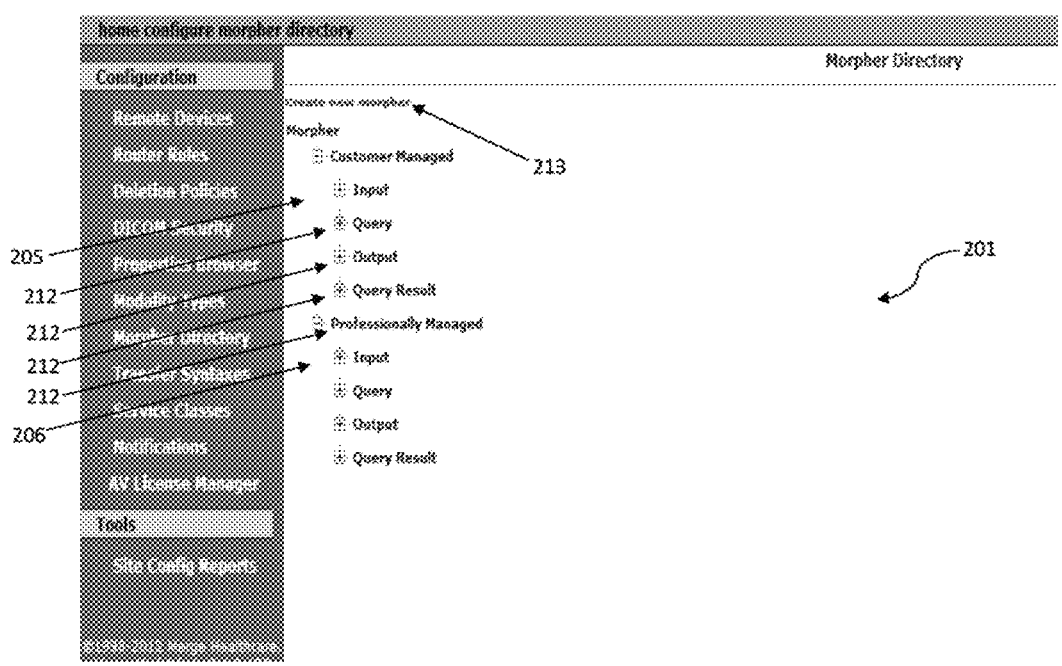
FIG. 2 is a screen shot illustrating a graphical user interface generated by the system of FIG. 1.

As noted above, the morpher application 131 interacts with a user to manage morphers. In some embodiments, the application 131 can create a GUI that allows a user to create new morphers and manage existing morphers. For example, FIG. 2 shows a management screen 201 of a GUI generated by the morpher application 131 that allows a user to manage existing morphers and create new morphers. The screen 201 can include selection mechanisms for selecting different categories of morphers. For example, the screen 201 can include a customer-managed morpher selection mechanism 205 and a professionally-managed morpher selection mechanism 206. A user can select the customer-managed selection mechanism 205 to access existing customer-managed morphers and create new customer-managed morphers. Similarly, a user can select the professionally-managed selection mechanism 206 to access existing professionally-managed morphers and create new professionally-managed morphers.

Professionally-managed morphers can include morphers created by individuals having detailed knowledge of a specific programming language (e.g., JAVA) as well as the DICOM standard and archiving fundamentals. For example, the professionally-managed morphers can be directly written by individuals in source code. In contrast, user-created morphers are morphers created by users through the application 131 and, in particular, through the GUI generated by the application 131 as described below. Therefore, user-created morphers insulate users who are creating or modifying the morpher from the internals of the archive and the specific programming used to code the morphers. Accordingly, the user-created morphers require minimal knowledge of the DICOM standard to be able to create and/or modify morphers. In some embodiments, only the user-created morphers are editable by a user through the application 131. In other embodiments, each user may be assigned different access, read, and write rights that govern what morphers the user may access and how the user can interact with (e.g., modify) such morphers.

Both the user-created morphers and the professionally-managed morphers can include further categories of morphers. For example, morphers can be categorized as an input morpher, a query morpher, an output morpher, or a query result. Input morphers are executed when an image is received at a data source 133, and output morphers are applied to images leaving a data source 133 (e.g., for transmission to and storage in a different data source). Query morphers are applied to queries performed for stored images within a data source 133, and query result morphers are applied to the results of a query performed for stored images within a data source 133. It should be understood that other categories of morphers can be used to handle other types of transactions performed with images or other data. Furthermore, in some embodiments, no categories of morphers are used. Also, in some embodiments, a user can access a directory of all existing morphers to locate morphers of interest (i.e., rather than drilling down through categories of morphers).

Figure 3:
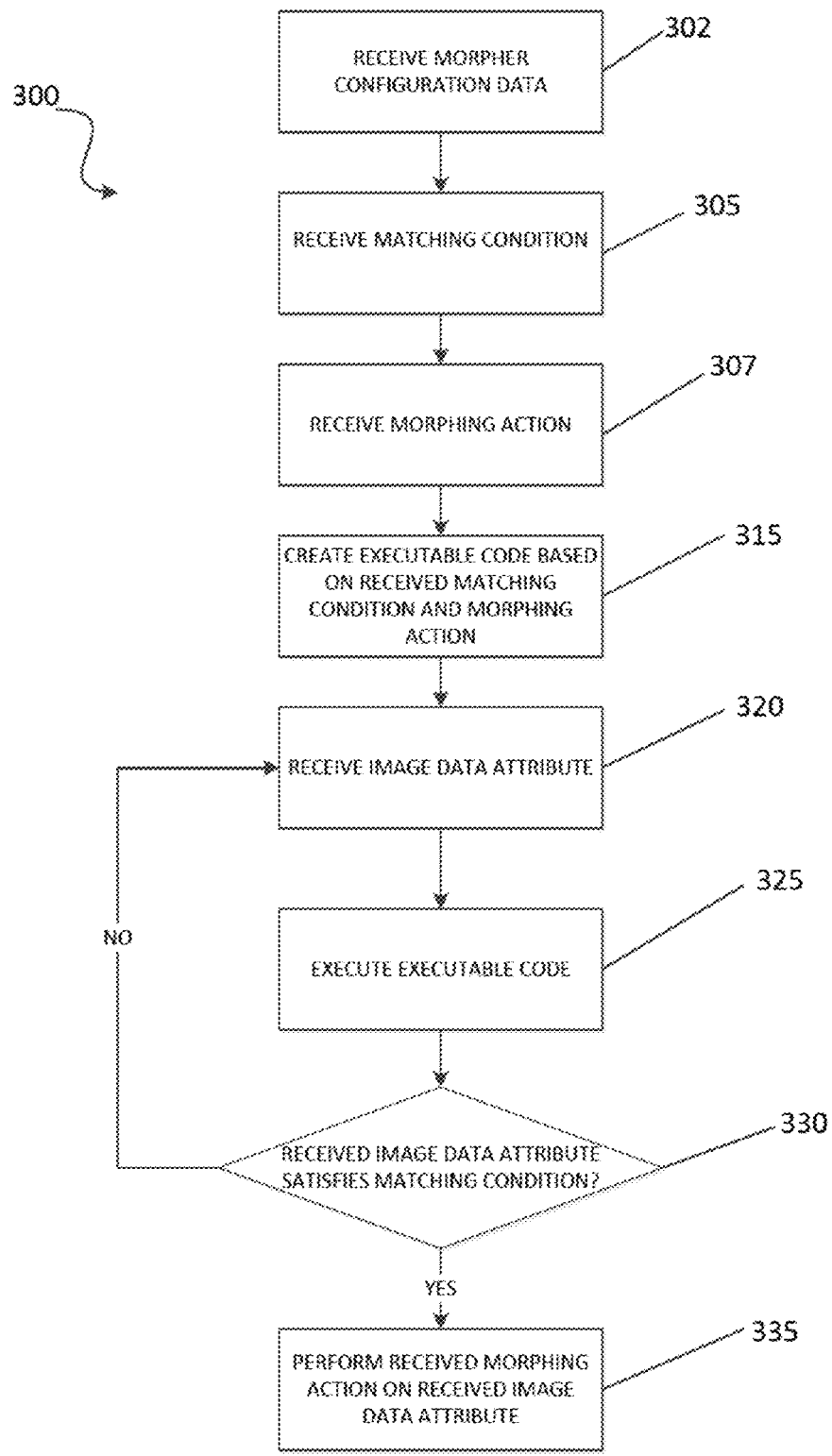
FIG. 3 is a flow chart illustrating a method of defining a morpher performed by the system of FIG. 1.

Each category of morpher can be associated with a create morpher selection mechanism 213 (see FIG. 2). A user can select the create morpher selection mechanism 213 to add a new morpher to the associated morpher category. In some embodiments, the application 131 also allows a user to create a new morpher without initially defining a category for the new morpher. FIG. 3 is a flowchart illustrating a method 300 performed by the morpher application 131 to create a new morpher. As shown in FIG. 3, to start the creation process, the application 131 receives configuration data for the new morpher (at block 302). For example, FIG. 4A displays a new morpher creation screen 400. The screen 400 includes various inputs that allow a user to provide configuration data for a new morpher. The inputs can include a morpher name input 401, a morpher description input 402, and a morpher type input 403. The screen 400 can also include an application entities ("AEs") input 404 that allows the user to select applications associated with the new morpher. In particular, a morpher can be configured to be applied only to data (e.g., images) supplied from particular application(s) (e.g., a query application, an output application, etc.). Therefore, a user can select the AEs for each new morpher. In some embodiments, the screen 400 includes a list of available AEs, and a user can use the list to identify and select one or more AEs for the new morpher. Alternatively, default AEs can be assigned to each new morpher.

Within the morpher creation screen 400, a user can also enable and disable the morpher, such as by selecting or unselecting a "Morpher is Enabled" checkbox 406. Additional information regarding enabled versus disabled morphers is provided below. Accordingly, the configuration data for the new morpher specifies identifying information for the morpher and the parameters in which the new morpher will be applied.

Figure 4A:
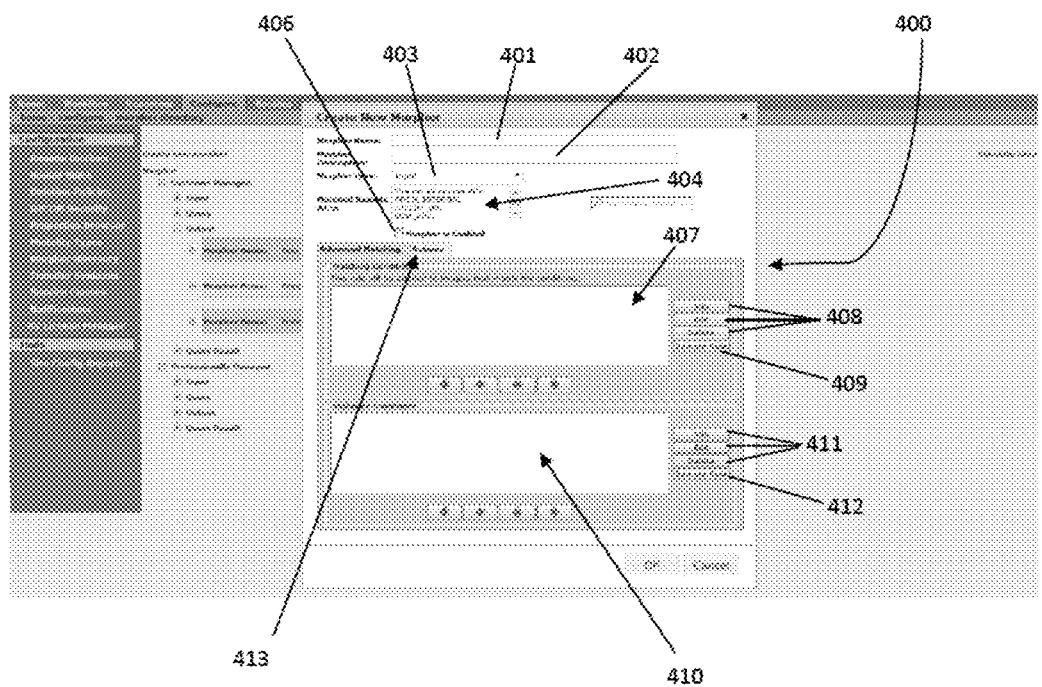
FIGS. 4A-C and 5-24 are screen shots illustrating a graphical user interface generated by the system of FIG. 1.
Figure 4B:
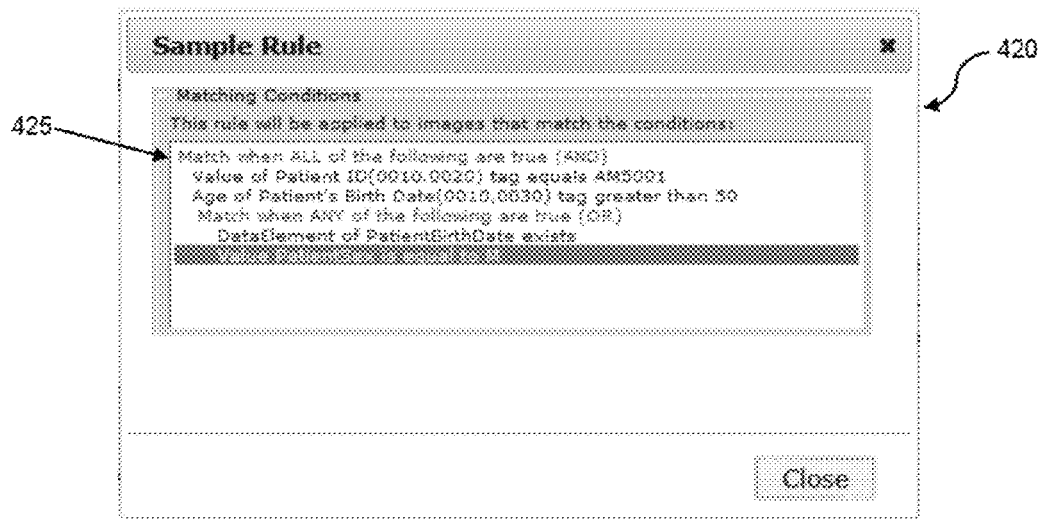

Returning to FIG. 3, the application 131 also receives one or more matching conditions for a new morpher (at block 305). For example, as illustrated in FIG. 4A, the morpher creation screen 400 also includes a matching conditions input 407. A user can add, edit, and delete matching conditions from the input 407 using one or more selection mechanisms 408. The input 407 can also be associated with a sample rule selection mechanism 409 that allows a user to view a sample matching condition. For example, as illustrated in FIG. 4B, the application 131 can generate a window 420 that displays a sample matching condition 425. In some embodiments, the sample matching condition 425 is based on input previously-provided by the user. In other embodiments, the sample matching condition 425 is unrelated to any input previously provided by the user (e.g., the condition 425 is a default condition displayed anytime the user selects the sample rule selection mechanism 409). Accordingly, in some embodiments, the application 131 prevents a user from modifying the sample matching condition 425. However, in other embodiments, a user can perform certain functions on the sample matching condition 425, such as copying the condition 425 or a portion thereof, editing the condition 425, etc.

A matching condition includes an argument, an operand, and an operator. In some embodiments, a matching condition evaluates to a "TRUE" value or a "FALSE" value. The argument specifies data used as an input to the operand. The operand specifies an operation applied to the argument, and the operator specifies operations performed on the output of the operand. An operator can be a unitary operator that operates on just the output of the operand (e.g., an is-empty operator) or a binary operator (e.g., a less-than or greater-than operator) that operates on the output of the operand in conjunction with operation data (e.g., constants, predetermined strings or datasets, etc.).

For example, an argument can include a DICOM tag, a DICOM sequence tag, or an item within a sequence. Similarly, an operand can include an age operand that calculates the days between a date and today's date, a data-element operand that extracts a data element from a dataset, a length operand that calculates the length of a value of an argument, a value operand that extracts the value of the image attribute, a value-representation ("VR") operand that extracts a value representation of an image attribute, or a value-multiplicity ("VM") operand that extracts the value multiplicity of an image attribute. For example, below is an example portion of a DICOM file represented in a human-readable format:

```
(0010,0010) <PN>              # 16, ((1)) PATIENTNAME
[CREST^MAGGIE^^^]
(0010,0030) <DA> [19760919]   # 8, ((1)) PATIENTBIRT
(0010,0040) <CS> [F]          # 2, ((1)) PATIENTSEX
....
(0018,1164) <DS> [0.20\0.20]  # 10, ((2)) IMAGERPIXELSPACING
```

Each line is a data element of the DICOM file. Each data element is identified by a tag, which includes a group and an element number. The tag is denoted within single parentheses, such as (0010, 0010). Each data element also includes a value representation (e.g., character string, name, integer, date, code, etc.). The value representation is denoted within the angle brackets "<" and ">," such as <PN>. For example, the "PATIENTBIRT" data element identified by the tag (0010, 0030) is in date or "DA" format, which can include an eight-digit data string formatted as "YYYYMMDD." The VR operand reads the value representation from a data element.

Each data element also includes a value multiplicity. The value multiplicity indicates whether a data element contains only value of its type or several values (e.g., how many values per attribute). The value multiplicity is denoted with the square brackets "[" and "[," such as [0.20/0.20]. If a data element has several values, the values listed in the value multiplicity are separated by backward slashes "\." The VM operand reads the number of values from the value multiplicity. For example, the "PATIENTNAME" data element identified by the tag (0010,0010) has a value multiplicity of [CREST^MAGGIE^^^], which includes only a single value (i.e., the value multiplicity does not include any backward slashes separating values. Therefore, the VM operand would return a value of "1" for the "PATIENTNAME" data element. In contrast, the "IMAGERPIXELSPACING" data element identified by the tag (0018,1164) has a value multiplicity of [0.20\0.20], which includes two values separated by a backward slash. Therefore, the VM operand would return a value of "2" for the "IMAGERPIXELSPACING" data element.

Furthermore, an operator can include, for example:
a contains operator that evaluates whether a substring matches another string,
an equals operator that evaluates whether one value is equal to another value,
an exists operator that evaluates whether a value exists in a dataset,
a greater-than operator that evaluates if one value is greater than another value,
a greater-than-or-equal-to operator that evaluates if one value is greater than or equal to another value,
an is-empty operator that evaluates if a value is empty or not,
an is-standard operator that verifies whether a value confirms to a standard definition,
a less-than operator that evaluates if one value is less than another value,
a less-than-or-equal-to operator that evaluates if one value is less than or equal to another value, and
a matches operator that performs regular expression matching.

For example, a matching condition can include an argument that includes a DICOM tag, an operand that extracts the value of the DICOM tag, and an operator that determines whether the extracted value of the DICOM tag is equal to a predetermined value. Similarly, a matching condition can include an argument that includes a DICOM tag, an operand that extracts the value of the DICOM tag, and an operator that determines whether the extract value of the DICOM tag matches a predetermined string.

Figure 5:
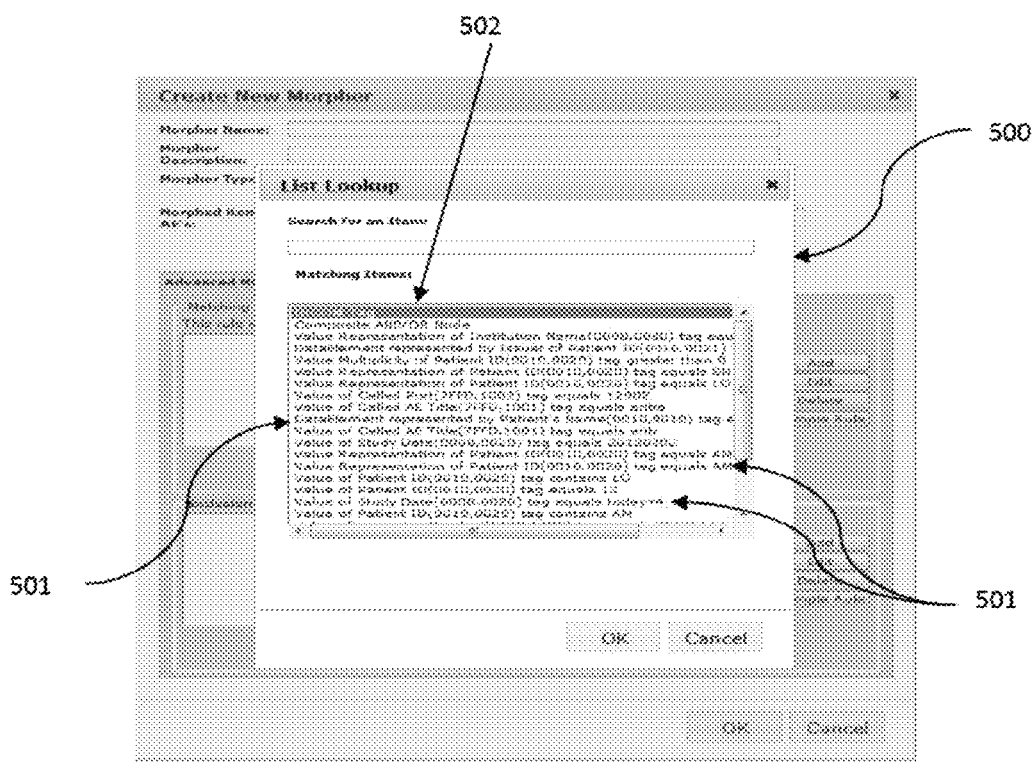

In some embodiments, a user can select a matching condition or elements thereof from a list or look-up table. For example, FIG. 5 illustrates a lookup window 500 displaying available matching conditions 501 in a list 502. If the user selects one of the available matching conditions 501 from the list 502, the application 131 adds the selected matching condition 501 to the input 407.

Figure 6:
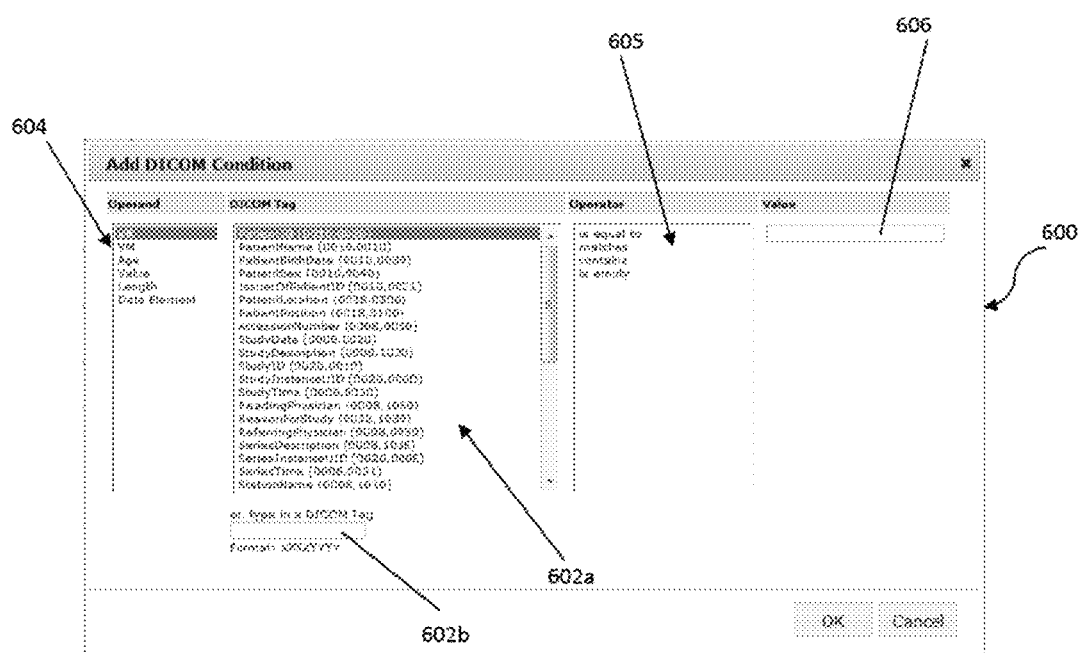

A user can also add a matching condition to the input 407 by selecting each element of the condition from lists of available options for each element. For example, if a user selects an "Add" selection mechanism 408 on the screen 400, the application 131 can display an add condition window 600 as illustrated in FIG. 6. A user can use the addition condition window 600 to select an argument (e.g., a DICOM tag) from an argument list 602a or enter an argument using an argument input 602b. A user can also use the window 600 to select an operand from an operand list 604, select an operator from an operator list 605, and, optionally, enter a value associated with the operator using a value input 606. After making the desired selections, the user selects the "OK" selection mechanism 607 and the application 131 automatically adds a matching condition to the input field 407 based on the user selections.

Figure 7:
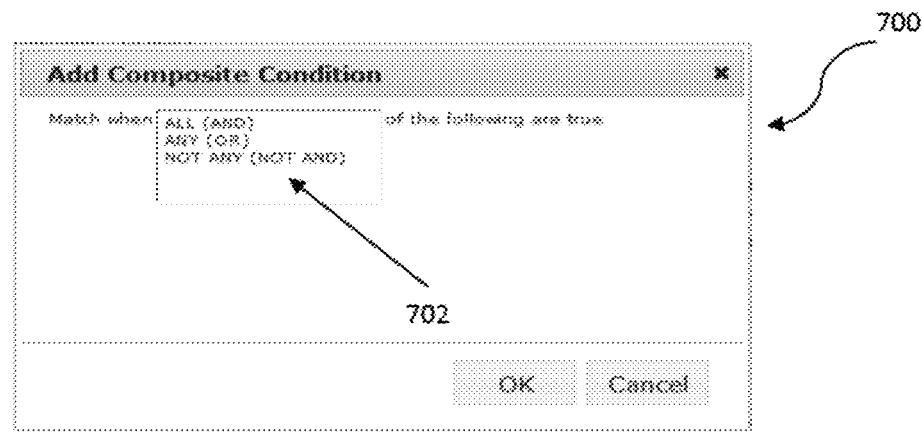
Figure 8:

In some embodiments, a user can define more than one matching condition to create a composite condition. A composite condition is composed of individual matching conditions that are connected together by logic operators, such as (in the case of a user entering more than one matching condition) user selection of two or more of the matching conditions to create a composite condition. For example, after selecting two or more matching conditions (e.g., within the input 407), the application 131 can display an add-composite-condition window 700 (see, e.g., FIG. 7). The add-composite-condition window 700 allows a user to tie two or more conditions together using a logic operator (e.g., AND, OR, NOT, etc.). In some embodiments, after grouping a set of matching conditions into a composite condition, the application 131 allows a user to tie the composite condition to other matching conditions or even other composite conditions. By creating a composite condition that has multiple levels, a user can create a powerful and effective matching condition for any situation. For example, FIG. 8 illustrates a sample composite matching condition 800. After creation, composite matching conditions can be illustrated in the input 407 (e.g., as illustrated in FIG. 8) like any other matching condition.

Figure 4C:
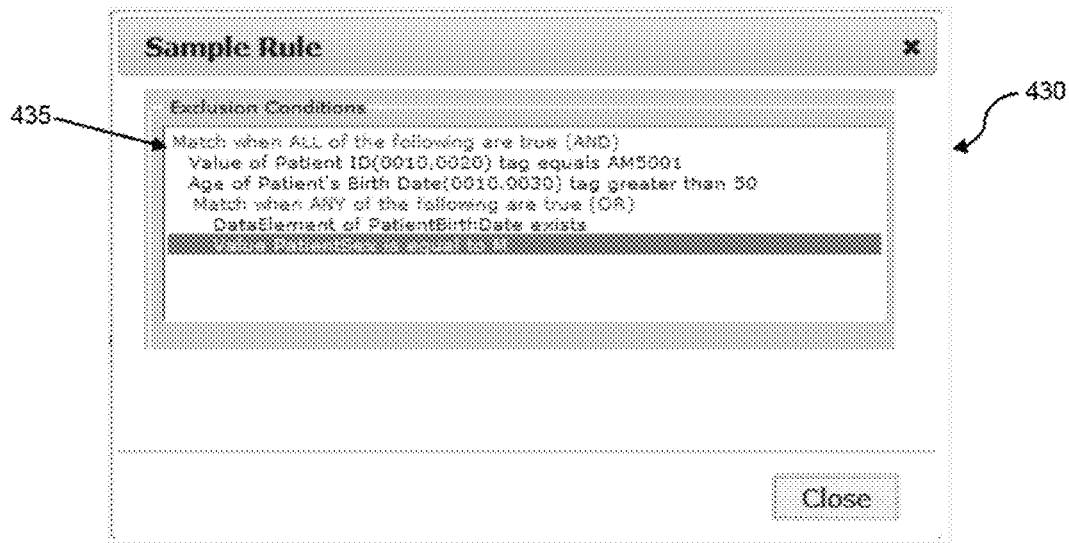

Optionally, similar to defining matching conditions, a user can use the morpher creation screen 400 (see FIG. 4A) to define exclusion conditions. Exclusion conditions exclude particular images that otherwise satisfy the matching condition(s) for a morpher. Exclusion conditions can be added, edited, and deleted using an exclusion conditions input 410 and selection mechanisms 411 as described above for the matching conditions. Similarly, a user can select a sample rule selection mechanism 412 that allows a user to view a sample exclusion condition. For example, as illustrated in FIG. 4C, the application 131 can generate a window 430 that displays a sample exclusion condition 435. In some embodiments, the sample exclusion condition 435 is based on input previously-provided by the user. In other embodiments, the sample exclusion condition 435 is unrelated to any input previously provided by the user (e.g., the condition 435 is a default condition displayed anytime the user selects the sample rule selection mechanism 412). Accordingly, in some embodiments, the application 131 prevents a user from modifying the sample exclusion condition 435. However, in other embodiments, a user can perform certain functions on the sample exclusion condition 435, such as copying the condition 435 or a portion thereof, editing the condition 435, etc.

Returning to FIG. 3, in addition to receiving one or more matching conditions, the application 131 also receives one or more morphing actions from the user (at block 307). The morphing action defines changes to make to an image (e.g., to one or more image attributes, which can include a patient identifier, a patient name, or an issuer of a patient identifier) when the image satisfies the corresponding matching conditions. Similar to a matching condition, a morphing action can include an operand, an argument, and an operator. The morphing action applies the operator to the results of applying the operand to the argument. For example, an argument for a morphing action can include a DICOM tag. An operand for a morphing action can include a construct operand that constructs a data element with a specified tag and a data-element operand that extracts a data element from a dataset. An operator for a morphing action can include, for example:

an add operator that adds two values,
a change operator that changes one or more specified attributes of a DICOM tag,
a copy operator that copies the value of a source DICOM tag into a destination tag,
a delete operator that deletes a DICOM tag from a dataset,
a divide operator that divides two values,
a flip operator that flips the values of two tags,
an inject operator that inserts a new tag into a dataset,
an insert operator that inserts the value at any index into another value,
a modify operator that modifies the attributes of a DICOM tag,
a replace operator that replaces the value of a source tag with the destination tag value,
a round operator that rounds a value (e.g., 10.7 is rounded to 11),
a subtract operator that subtracts two values, and
a truncate operator that truncates a value to a specified length.

Figure 9:
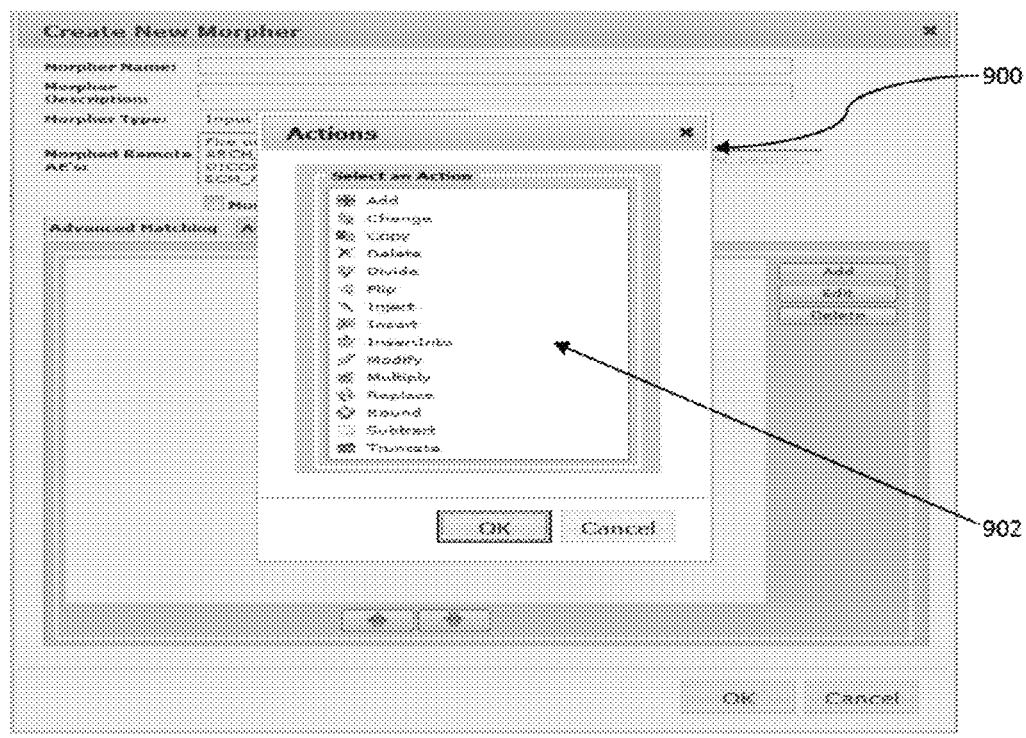
Figure 10:
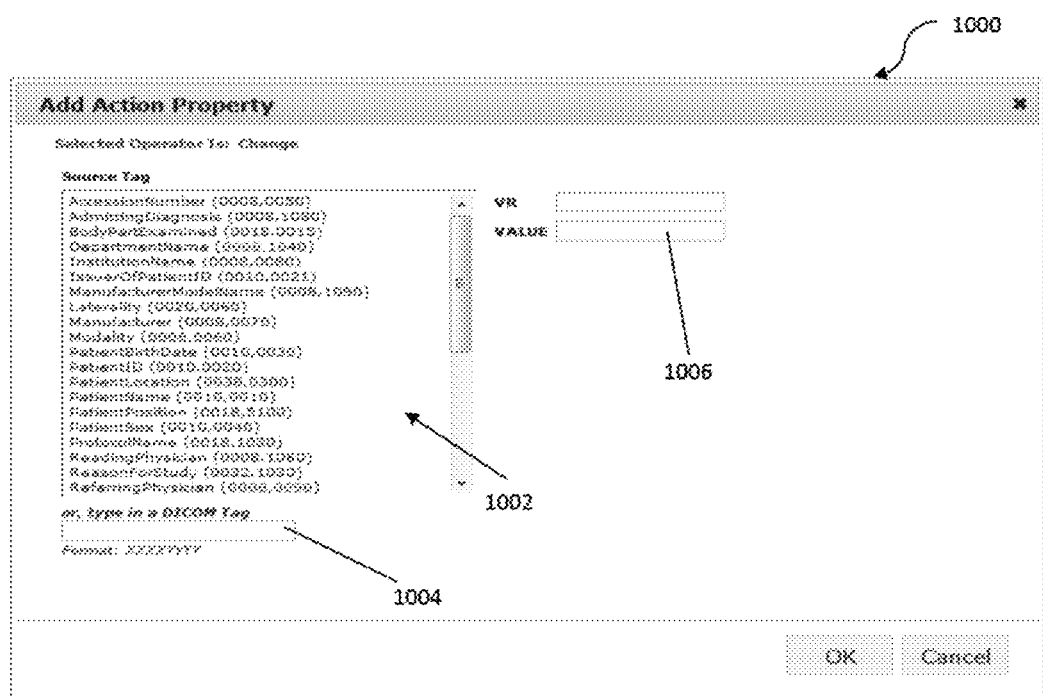

In some embodiments, a user can use the morpher creation screen 400 to input the morphing action for a new morpher. For example, a user can select an "Actions" tab 413 (see FIG. 4) on the screen 400 to access an action input that operates similar to the matching condition input 407. For example, if a user wants to add a morphing action, the user can select an "Add" selection mechanism to access an action selection window 900 as illustrated in FIG. 9. The window 900 can include an actions list 902 that lists available actions or operators. After selecting an action from the window 900, the application 131 can display a property window 1000 as illustrated in FIG. 10. The property window 1000 allows a user to select the source argument (e.g., a DICOM tag) using a list of available tags 1002. Alternatively, a user can manually enter a tag into a tag input 1004. Additionally, if the user-selected action is associated with a value (e.g., add 5 to value of a tag), a user can manually enter the value using a value input 1006.

In some embodiments, a user can define a composite morphing action. A composite morphing action includes two or more morphing actions. When a user specifies a composite morphing action, each morphing action included in the composite morphing action is applied when the corresponding matching condition(s) are satisfied.

Returning to FIG. 3, after receiving matching condition(s) and morphing action(s) from the user for a new morpher, the application 131 automatically creates a morpher (i.e., executable code) based on the received matching condition(s) and morphing action(s) (at block 315). As noted above, in some embodiments, the application 131 includes a rules engine and a morphing core wherein the rules engine is configured to create morphers. In some embodiments, the rules engine codes the morphers in a specialty morpher or rules language. In this morpher language, matching conditions and morphing actions can have the following structure, by way of example only:

DICOM(Operand(ArgumentType:ArgumentValue)
Operator OperationData)

where "DICOM" is a keyword for the language specifying a DICOM Condition or DICOM Action, "Operand" is the object of an operation, a quantity on which an operation (defined by an operator) is performed, "ArgumentType" specifies a classification identifying the various types of data that can be used as an input for the operand, "ArgumentValue" specifies input data for an operand to function on, "Operator" specifies the operations that can be performed on the results of the operand using operation data (as described above)—and can include a unary operator or a binary operator, and "Operation Data" specifies data used to perform an operation in conjunction with an operand.

Examples of matching conditions and morphing actions using an example morpher language are provided below. In particular, exemplary matching conditions can include the executable code illustrated by cases 1-3, below:

Case 1: Standalone DICOM Condition with Unary Operator

DICOM(DATAELEMENT(TAG:00280008)EXISTS)

where "DICOM" is a reserved keyword for the morpher language, "DATAELEMENT" specifies the DATAELEMENT operand which extracts from a given dataset represented by the Argument Value and is a reserved keyword, "TAG" specifies the Argument Type and is a reserved keyword. "0028008: specifies the Tag represented by group number (0028) and part number (0008). This tag will be evaluated by the DATAELEMENT operand and is extracted from the dataset. "EXISTS" represents the exists operator, which is a unary operator and checks for the existence of the tag specified in the Argument Value in a given dataset. Again, "EXISTS" can be a reserved keyword.

Case 2: Standalone DICOM Condition with Binary Operator

DICOM(VALUE(TAG:00280008)="0")

where "DICOM" is a reserved keyword and "VALUE" specifies the value operand, which extracts the value of given tag. "TAG" specifies the Argument Type and is also a reserved keyword. "0028008" specifies the Tag represented by group number (0028) and part number (0008). This tag will be evaluated by the VALUE operand to extract its value. "=" represents the equals operator and compares the value extracted by the VALUE operand to the value specified in the operation data. If both values match, the equals operator returns TRUE. Otherwise, if the values do not match, the equals operator returns FALSE. Like other operators, "=" is a reserved symbol for the morpher language. Finally, "0" specifies the operation data for the equals operator.

Case 3: Composite DICOM Conditions

AND(DICOM(DATAELEMENT(TAG:00280008)
exists),

DICOM(VALUE(TAG:00280008)="0"))

As noted above, a composite matching condition is composed of individual matching conditions and/or other composite matching conditions connected together by a logic operation (e.g., AND, OR, NOT, etc.). Therefore, a composite matching condition can have one of the following formats:

AND(Term$_1$, Term$_2$, . . . Term$_n$)

OR(Term$_1$, Term$_2$, . . . Term$_n$)

NOT(Term$_1$, Term$_2$, . . . Term$_n$)

where "Term$_n$" is a matching condition or a composite condition and AND, OR, NOT are reserved keywords for the morpher language.

Similar to the sample matching conditions, exemplary morphing actions are illustrated by cases 4-6 below:

Case 4: Standalone DICOM Action

DICOM(DATAELEMENT(SOURCETAG:00280008) DELETE)

where "DICOM" is a key word, "DATAELEMENT" is an operand that extracts the data element represented by the argument value in the dataset and is a reserved keyword for the morphing language, and "SOURCETAG" is another key word, and specifies the Argument Type. As noted above, "0028008" specifies the tag represented by group number (0028) and part number (0008). "DELETE" represents the unary delete operator that deletes the tag represented by the Argument Value in the dataset, and is a reserved keyword for the Language.

Case 5: DICOM Action with Binary Operator and Operation Data

DICOM(DATAELEMENT(SOURCETAG:00100020) FLIP DESTINATIONTAG:"00280080")

where "DICOM" is a key word and "DATAELEMENT" is an operand that extracts the data element represented by the argument value in the dataset and is also a reserved keyword. "SOURCETAG" specifies the Argument Type and is a reserved keyword, and "0010020" specifies the Tag represented by group number (0010) and part number (0020). As noted above, "FLIP" represents the binary Flip operator that flips the value of the source tag with the value of the destination tag. "DESTINATIONTAG" specifies the Operation Data Type and is a reserved keyword, and "0028008" specifies the tag represented by group number (0028) and part number (0080).

Case 6: Composite DICOM Action

DICOM(DATAELEMENT(SOURCETAG:00100020) FLIP DESTINATIONTAG:"00080080"),

DICOM(DATAELEMENT(SOURCETAG:00181318) ROUND)

As noted above, a composite morphing action is composed of individual DICOM Actions and can be separated by commas. Therefore, a composite morphing action can have the following format:

Term$_1$, Term$_2$, . . . Term$_n$ where "Term$_n$" is a morphing action.

Just like other large and small programming languages, the morpher language can be supported by a grammar. A grammar is a set of structural rules that govern the composition of phrases and words in a given language. The morpher language can be associated with a parser and a syntax tree builder (e.g., using Java Compiler Compiler ("JavaCC") and Java Tree Builder ("JTB"), respectively, and passing each component a grammar file associated with the morpher language). JTB (see http://compilers.cs.ucla.edu/jtb/) is a syntax tree builder used with the JavaCC parser generator. The JTB takes a JavaCC grammar file as input and automatically generates the following:

a set of syntax tree classes based on the productions in the grammar, utilizing the visitor design pattern, a visitor interface and a GJVisitor interface, a DepthFirstVisitor depth-first visitor and a GJDepthFirst depth-first visitor, whose default methods visit the children of a current node, and a JavaCC grammar (jtb.out.jj) with annotations to build the syntax tree during parsing.

JavaCC (see http://javacc.java.net/) is a parser generator for use with Java applications. A parser generator is a tool that reads a grammar specification and converts it to a Java program that can recognize matches to the grammar. In addition to the parser generator itself, JavaCC provides other standard capabilities related to parser generation such as tree building (via a tool called JJTree included with JavaCC), actions, debugging, etc.

Morphing conditions and morphing actions abstract syntax tree walkers are also created within the rules engine by implementing the Visitor Design Pattern. These tree walkers traverse the syntax tree created by JTB for morphing conditions or morphing actions by going to each token node and creating an object hierarchy structure that can be used by the morphing core when initializing and executing a morpher.

It should be understood that the rules engine can be designed in such a way that it is extendable to other areas within the vendor neutral archive and other Java-based products, and is not limited to being implemented or used using the JAVA language or associated products.

After the rules engine creates a morpher, the morpher can be executed (i.e., applied to received image data). In some embodiments, a generated morpher is applied by the application 131. However, it should be understood that in some embodiments a separate application executes generated morphers. For example, in some embodiments, the application 131 receives image data (at block 320) and executes existing and enabled morphers to apply the morphers to the image data (at block 325). Receiving image data can include receiving an image that is associated with one or more image attributes. The received image can be received from a data source 133, searched for (queries) in a data source 133, returned as a search result from a data source, or transmitted to a data source 133. The way an image is received can define the type of morphers applied to the image. In particular (and as described above), morphers can be grouped into an input morpher category, a query morpher category, an output morpher category, and a query result morpher category by way of example.

In some embodiments, the morphing core is responsible for initialization and execution of a morpher. In particular, and with reference to java programming language by way of example only, the rules engine, when called by the morphing core upon initialization of a morpher, returns a java object hierarchy tree representation of a morpher (different from the abstract syntax tree representation) to the morphing core. The java object hierarchy tree representation returned by the rules engine is then used by the morphing core to execute a morpher based on the occurrence of specific events (e.g., when DICOM images coming from a designated source are injected into a data source 133 or sent out of a data source 133, as part of a data query, etc.).

The morphing core executes a morpher to determine if the received image data satisfies the matching conditions associated with the morpher (at block 330). In other words, the application 131 determines if a value of an image attribute of the received image data satisfies the matching condition. If the value of the image attribute does not satisfy the specified matching condition, the morphing action associated with the morpher is not performed. However, if the value of the image attribute satisfies the specified matching condition, the morpher core performs the corresponding specified morphing action on the image (at block 335). In particular, the morphing core can automatically perform the morphing action by modifying a value of at least one attribute of the received image. It should be understood that the image attribute modified according to the morphing action can be the same or different than the image attribute used with the matching condition. It should also be noted that the morphing core can be designed to be backwards compatible. Therefore, the morphing core can initialize and execute legacy morphers (e.g., created using previous versions or configurations of the morpher language).

Figure 11:
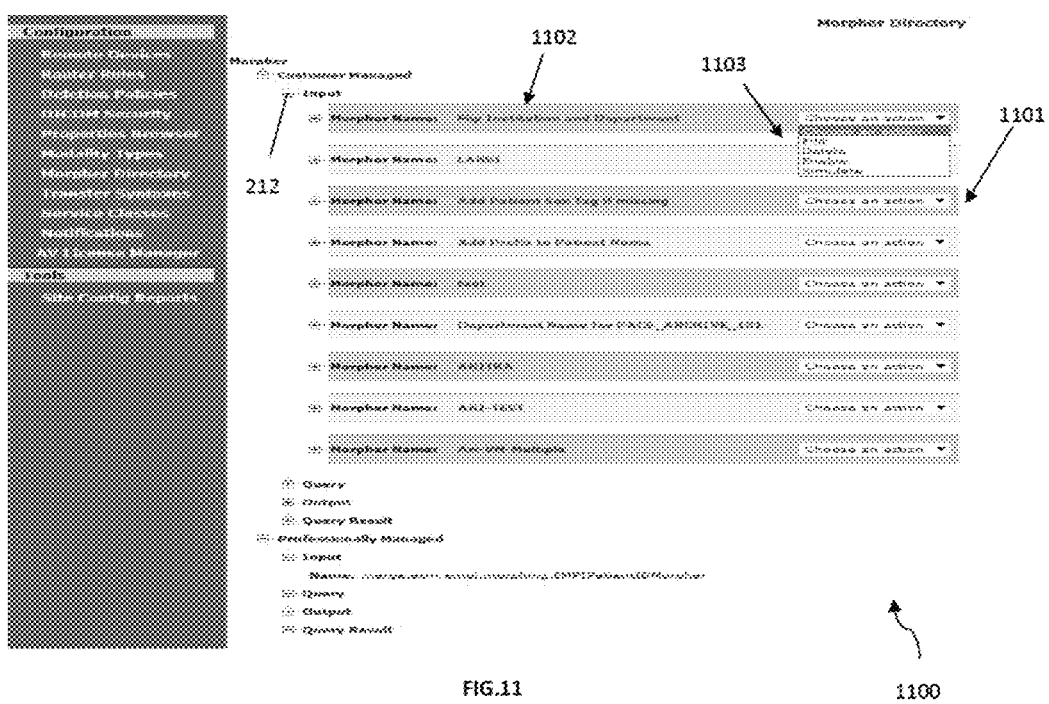
Figure 12:
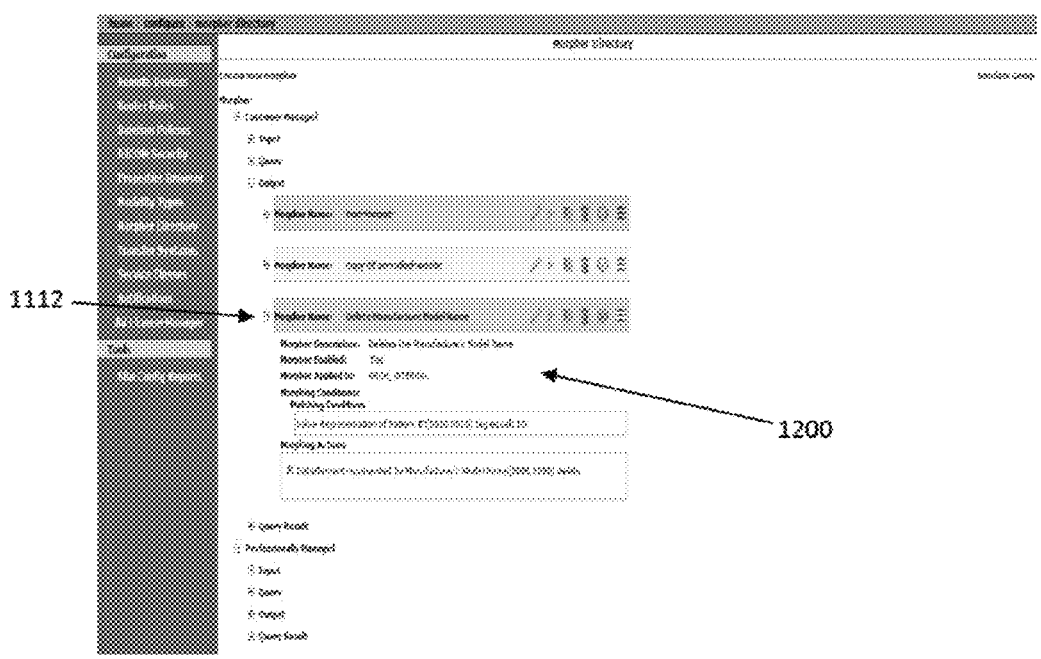

As noted above, the application 131 can be used to create new morphers and manage existing morphers. In particular, and as illustrated in FIG. 2, each category of morphers can include an expand selection mechanism 212 that a user can select to view and manage the associated category of morphers. For example, FIG. 11 illustrates the screen 1100 that is displayed after a user selects the expand selection mechanism 212 for the input morpher category. As illustrated in FIG. 11, selecting the expand selection mechanism 212 for a particular category causes the GUI to display a list 1101 of existing morphers for the category. Each existing morpher can be identified by a morpher name 1102 (e.g., "Flip Institution and Department"). In some embodiments, as illustrated in FIG. 12, a user can select the name of an existing morpher (or select an expand selection mechanism 1112 associated with each existing morpher) to view details 1200 about the morpher, such as the matching conditions and morphing actions for the morpher, a description of the morpher, an indication of whether the morpher is enabled or disabled, a designation of what data source(s) (e.g., application(s)) the morpher is associated with, etc.

For each existing morpher, a user can use the GUI to access a menu 1103 of available options for the morpher. As illustrated in FIG. 11, the menu 1103 can allow a user to edit, delete, enable, disable, simulate, copy, prioritize, export, and/or input a morpher. Editing a morpher can include allowing the user to modify the matching condition and/or the morphing action (described below in more detail with respect to creating a new morpher). Editing an existing morpher in this manner is similar to creating a new morpher as described below. Editing a morpher can also include displaying source code to the user associated with the morpher and allowing the user to directly modify the code. In some embodiments, users may require particular write rights to directly modify morpher code.

Figure 13:
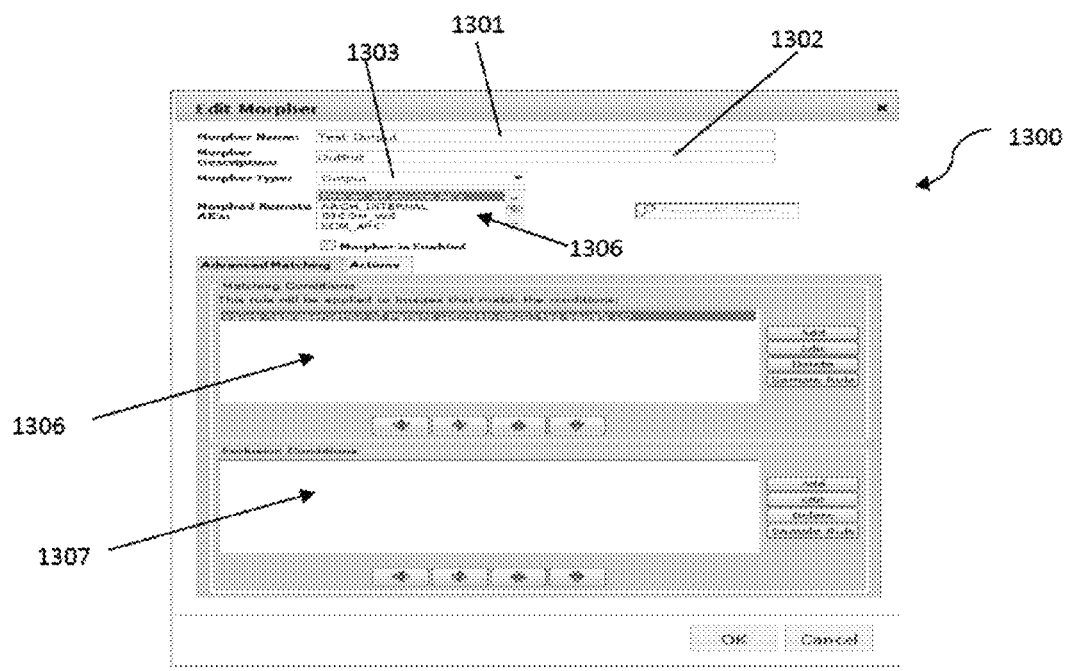
Figure 14:
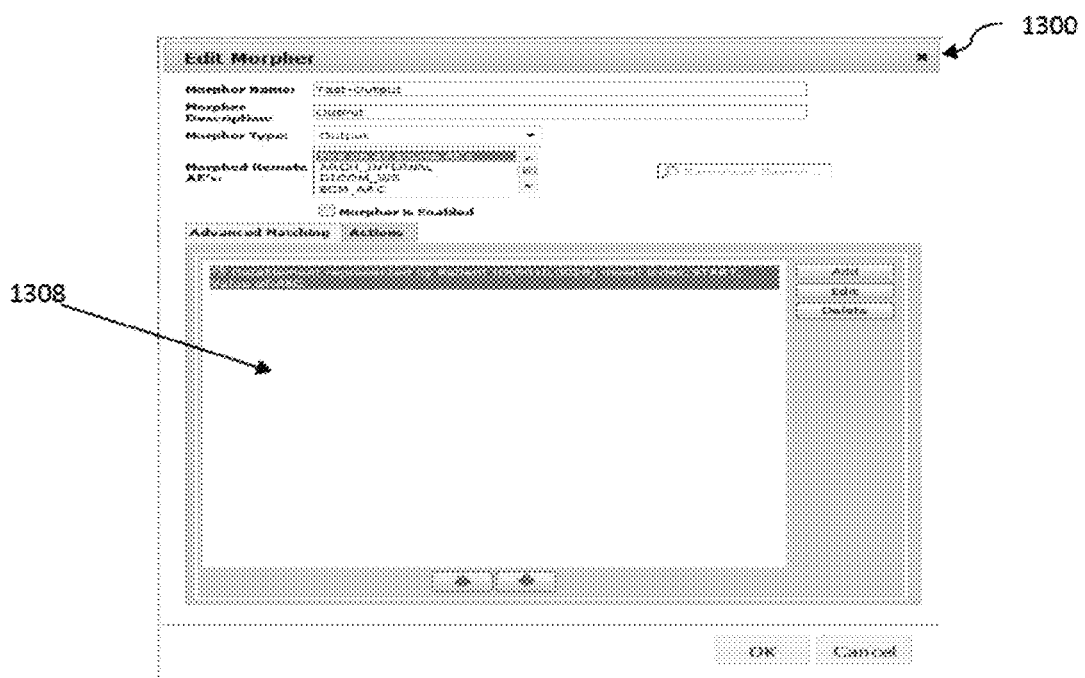

In some embodiments, editing an existing morpher is performed similar to creating to a new morpher. For example, FIGS. 13 and 14 illustrate a morpher edit window 1300. Similar to the screen 400, the window 1300 includes a name input 1301, a description input 1302, a type input 1303, an AE input 1304, a matching conditions input 1306, and an exclusion conditions input 1307. As illustrated in FIG. 14, the screen 1300 also includes a morphing actions input 1308. A user can use these inputs to modify a morpher's configuration data, matching conditions, and/or morphing actions.

Deleting a morpher removes the morpher from the list of existing morphers. In some embodiments, deleting a morpher can delete the morpher temporarily (such that the morpher is only deleted from the list of morphers but is still stored elsewhere) or permanently (such that the morpher is deleted from both the list of morphers and a stored location).

In some embodiments, rather than deleting a morpher, a user may desire to disable the morpher, which retains the morpher in the list of existing morpher but marks the morpher as being disabled (i.e., not being applied to image date). Disabling a morpher causes the morpher to remain inactive despite the matching condition being met, such that the morpher is not applied to any image attributes while disabled. For example, a user might disable a morpher to place that morpher on hiatus, such as to enable a different morpher for modifying image attributes having the same matching condition. This can be done, for example, to provide various potential morphing actions for the same matching condition without having to frequently update existing morphers. Further, a user may wish to disable a morpher whose actions conflict with those of another morpher. For example, two morphers may have the same matching condition, but opposing actions (e.g., one is configured to add certain information while the other is configured to delete that information). In such cases, a user may wish to disable one of the conflicting morphers without permanently deleting it, such that the disabled morpher can be used again in the future.

After disabling a particular morpher, a user can re-enable the morpher. Enabling a morpher allows that morpher to be applied to an image attribute when the corresponding matching condition is met. As illustrated in FIG. 12, in some embodiments, an existing morpher is listed or displayed differently based on whether the morpher is currently enabled. For example, enabled morphers can be displayed in a different color (e.g., dark gray) than disabled morphers (e.g., light gray). Alternatively or in addition, disabled morphers can be displayed in a different font or style (e.g., strikethrough) than enabled morphers.

Figure 15:
Figure 16:
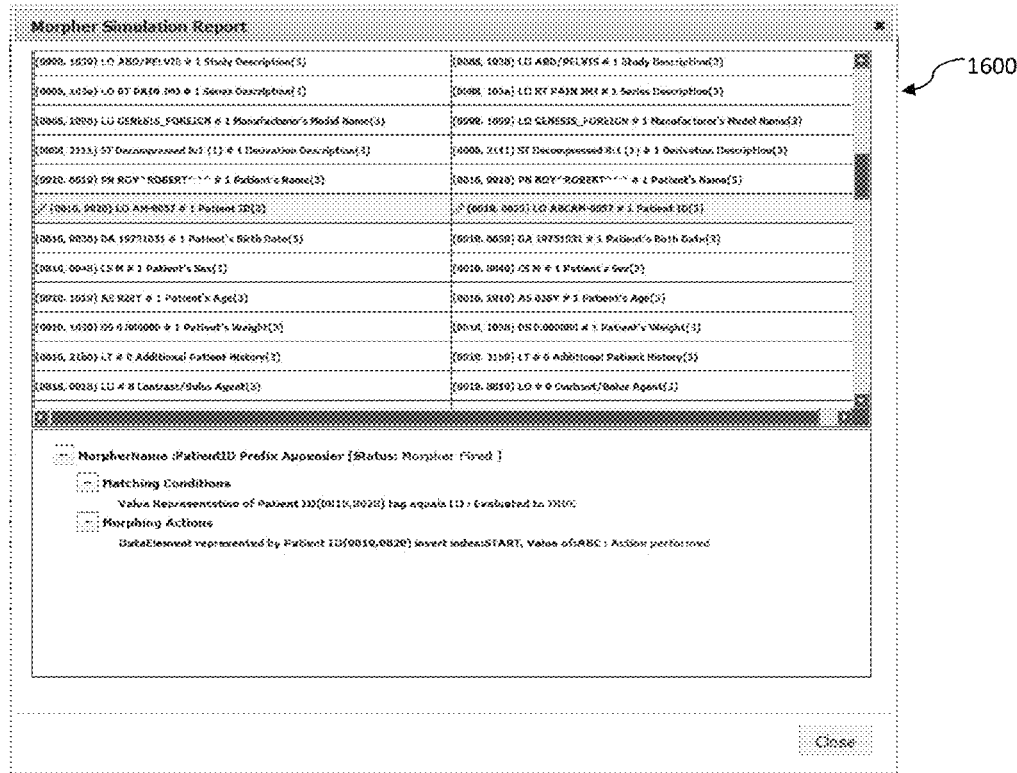
Figure 17:
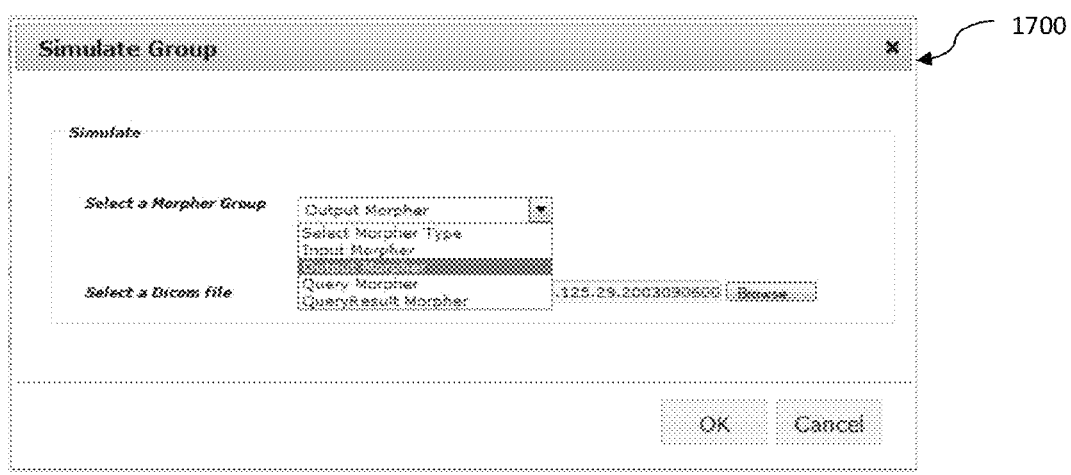
Figure 18:
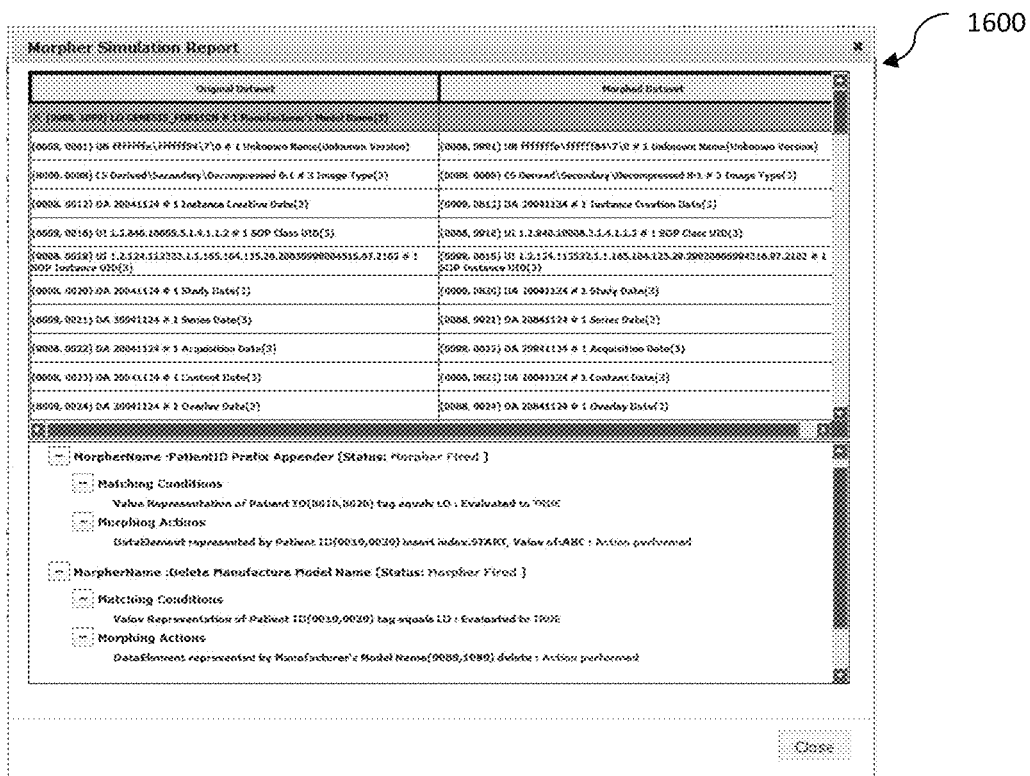
Figure 19:
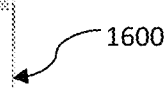

Simulating a morpher allows a user to test or simulate the functionality performed by a particular morpher on a given dataset (e.g., sample image data). In some embodiments, the application 131 is configured to generate a simulation report at the end of each simulation that enumerates the results of a simulation on a dataset (e.g., a DICOM dataset). The simulation can be performed in memory so the specified dataset on disk is not changed. In some embodiments, as part of running a simulation, the user can select the dataset (e.g., the DICOM file) for the simulation to use via a simulate morpher window 1500, as illustrated in FIG. 15. After running the simulation, the system can generate a simulation report 1600, as illustrated in FIG. 16. The simulation report 1600 identifies which tags were edited, which matching conditions of the simulated morpher were matched, and which actions were performed on the selected dataset. In some embodiments, the system also allows a user to simulate a group of morphers (by selecting a simulate group selection mechanism). For example, FIG. 17 shows a file selection window 1700 for simulating a morpher group. As with simulating a single morpher, simulation reports can be generated for each group of morphers simulated. For example, FIGS. 18 and 19 illustrate simulation reports 1600 for two different simulations performed on two different groups of morphers.

Copying a morpher makes a copy of an existing morpher which can be used as the starting point for a new morpher. The new copied morpher can be added to the list of existing morphers (e.g., for the same category as the original morpher). In some embodiments, the copied morpher can be associated a default name (e.g., a name including the name of the original morpher). The copied morpher can have the same matching condition and/or morphing action as the original morpher. Accordingly, if a user wants to create a morpher that performs the same or a similar morphing action and/or checks for the same or a similar matching condition as an existing morpher, a user can copy the existing morpher and modify the copied morpher as necessary.

In some embodiments, morphers can be prioritized. For example, in some embodiments, the order that existing morphers are displayed under a particular category designates the order in which the morphers are applied in practice. Accordingly, in some embodiments, existing morphers listed on the screen 1100 can be prioritized by clicking on an existing morpher and dragging the morpher to a desired place within the list of existing morphers.

Figure 20:
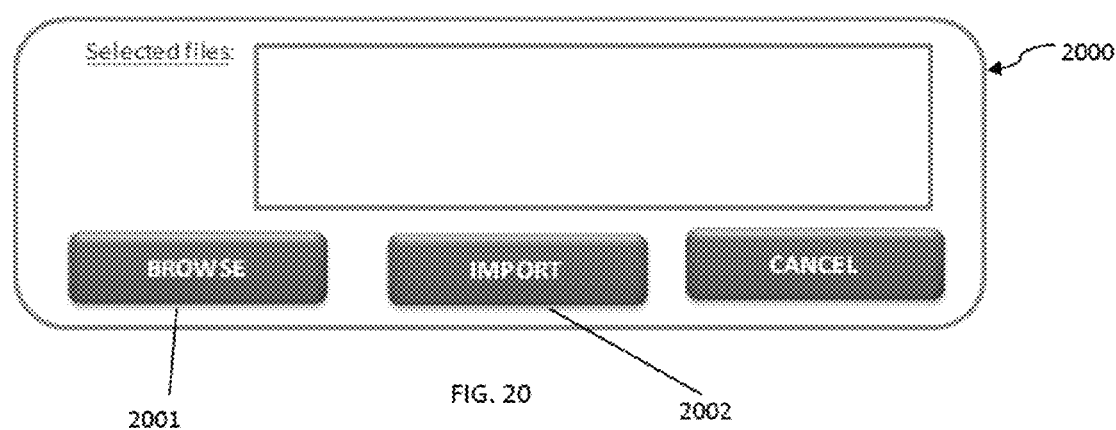
Figure 21:
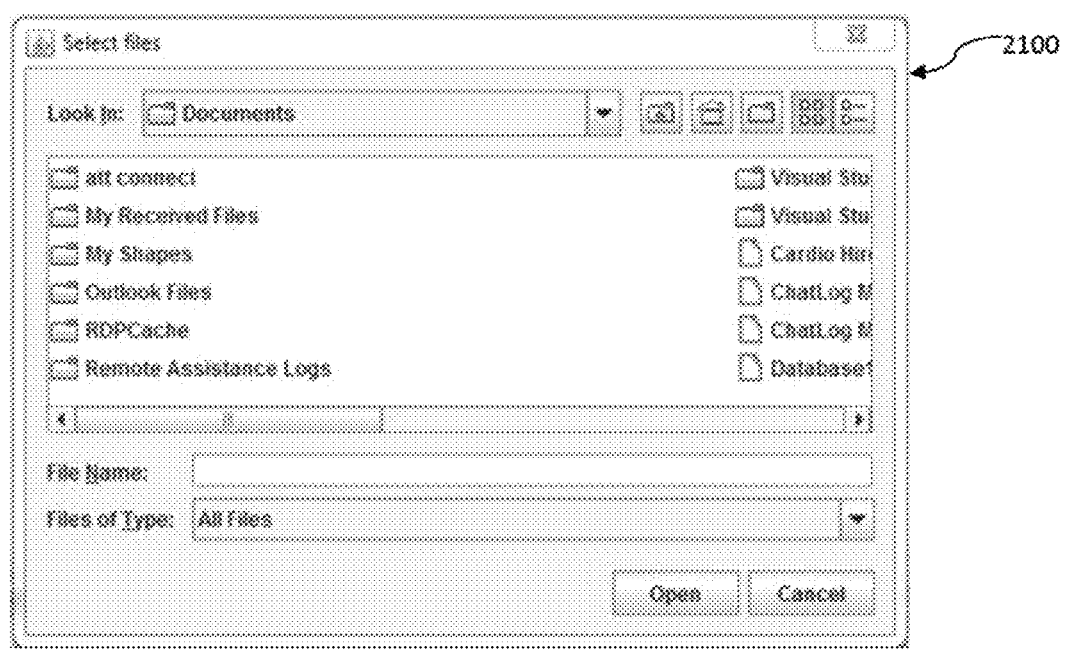
Figure 22:
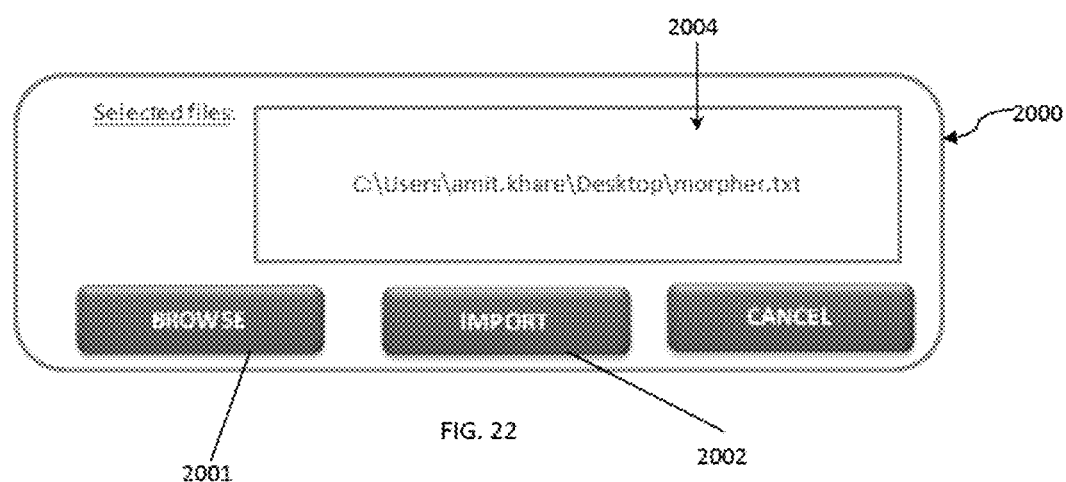

In some embodiments, the application 131 also allows a user to import and export morphers. In particular, an existing morpher managed through the application 131 can be written to a flat file or another storage location/type. Morphers can also be imported to the application 131 (e.g., as a flat file). For example, FIGS. 20-22 illustrate windows that can be presented to a user for importing morphers. In particular, FIG. 20 illustrates a dialog box 2000 that includes a browse selection mechanism 2001 and an import selection mechanism 2002. Selecting the browse selection mechanism 2001 opens a file selection window 2100 to help the user select the desired import file (see FIG. 21). When the user selects one or more files for importation, the selected files are in an input field 2004 of the dialog box 2000 (see FIG. 22). Selecting the import selection mechanism 2002 imports the displayed files to the memory 120 or another storage location associated with the application 131 and responsible for storing morphers.

Figure 23:
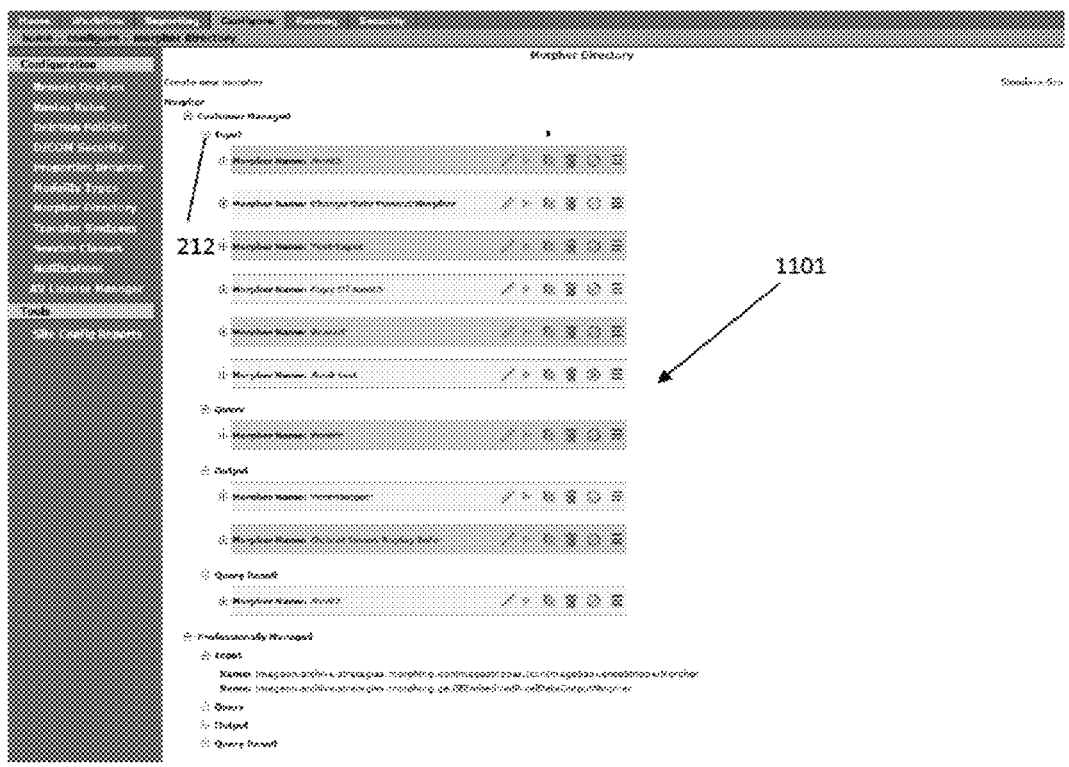
Figure 24:
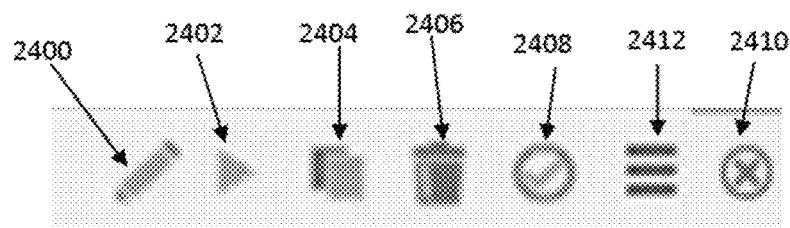

As illustrated in FIGS. 23 and 24, in some embodiments, some or all of the functions available for existing morphers are provided as selection mechanisms (e.g., icons) in place of or as an alternative to the drop-down menu 1103. For example, as illustrated in FIGS. 23 and 24, each existing morpher can be associated with an edit icon 2400, a simulate icon 2402, a copy icon 2404, a delete icon 2406, an enable icon 2408, a disable icon 2410, and a prioritize icon 2412.

It should be understood that, in some embodiments, the functionality of particular drop-down menu selections or selection mechanisms can be customized based on user preferences (e.g., automatically deleting morphers temporarily vs. permanently, simulating a morpher based on a predetermined data set, placing a copy of a morpher into a particular category and/or priority, etc.).

Thus, embodiments of the present invention provide, among other things, systems and methods for allowing users to define and manage morphers within the medical imaging industry. It should be understood that the functionality of the systems and methods described herein can also be used for other types of medical image processing, such as prefetching and hanging protocols ("HPs"). An HP is a set of rules for arranging images for optimal softcopy viewing within a picture archiving and communication system ("PACS") context. For example, one goal of an HP is to increase a radiologist's efficiency by eliminating the time otherwise required by the radiologist to manually reorder of the images for viewing and diagnosis. HPs also ensure consistent presentation of images for a particular type of study. HPs can vary based on modality, body part, department, personal preference, etc. A common interface (e.g., a common GUI), however, can be used for these different types of images processing, which increases ease of use and efficiency of the systems and methods. In addition to HP applications, other medical industry-related applications of the functionality can include; rule creation for medical image routing, creation and execution of image deletion policies, creation of image decompression rules, reassignments, HL7 mapping/morphing, XDS family of standards transfer mappings/morphing, ANSI interchange standard for patient monitoring and telemetry, desktop application interfaces (e.g., mapping of context and operations between multiple applications), and various point-to-point communications schemes. Similarly, it should be understood that the functionality can be used outside of the medical imaging industry.

Various features of the invention are set forth in the following claims.

What is claimed is:

1. A method of processing images to unify image data attributes of the images stored in an image repository using user-configurable morphers, the method comprising:
    generating, by a processor, a graphical user interface for display to a user;
    receiving, by the processor, a matching condition from the user through the graphical user interface;
    receiving, by the processor, a morphing action from the user through the graphical user interface, the morphing action including an action to perform on a data attribute associated with image data when the image data satisfies the matching condition;
    automatically creating, by the processor, executable code based on the morphing action and the matching condition and storing the executable code;
    for each new image received for storage in the image repository,
        automatically executing the stored executable code to compare the new image to the matching condition, and
        when the new image satisfies the matching condition, automatically performing the morphing action on the new image to generate a morphed version of the new image and store the morphed version of the new image to the image repository;
    receiving, by the processor, an update through the graphical user interface, the update including at least one of an updated matching condition and an updated morphing action;
    automatically creating, by the processor, updated executable code based on the update and storing the updated executable code; and
    for each new image received for storage in the image repository after receiving the update, automatically executing the stored updated executable code.

2. The method of claim 1, wherein receiving the morphing action includes receiving an action to perform on a data attribute including at least one selected from the group consisting of a patient identifier attribute, a patient name attribute, and an issuer of a patient identifier attribute.

3. The method of claim 1, wherein automatically performing the morphing action on the new image includes automatically modifying a value of a data attribute of the new image.

4. The method of claim 1, wherein automatically executing the stored executable code to compare the new image to the matching condition includes automatically executing the stored executable code to determine if a data attribute of the new image has a value.

5. The method of claim 1, wherein automatically executing the stored executable code to compare the new image to the matching condition includes automatically executing the stored executable code to determine if a value of a data attribute of the new image falls within a predetermined range of values.

6. The method of claim 1, wherein automatically executing the stored executable code to compare the new image to the matching condition includes automatically executing the stored executable code to determine if a value of a data attribute of the new image matches a predetermined value.

7. The method of claim 1, wherein the new image includes a medical image.

8. The method of claim 1, wherein automatically creating the executable code includes automatically creating the executable code in a rules language.

9. The method of claim 1, wherein receiving the matching condition includes receiving a composite condition.

10. The method of claim 1, wherein receiving the update through the graphical user interface includes
displaying the executable code to a user, and
allowing the user to modify the executable code.

11. The method of claim 1, wherein receiving the matching condition includes receiving a selection of the matching condition from a list of available matching conditions displayed as part of the graphical user interface.

12. The method of claim 1, wherein receiving the morphing action includes receiving a selection of the morphing action from a list of available morphing actions displayed as part of the graphical user interface.

13. The method of claim 1, further comprising receiving a selection from the user through the graphical user interface to disable the executable code and, in response to the selection, preventing the executable code from being executed against each new image received for storage in the image repository without deleting the executable code.

14. The method of claim 13, further comprising receiving a second selection from the user through the graphical user interface to enable the disabled executable code and, in response to the second selection, allowing the executable code to be executed against each new image received for storage in the image repository.

15. The method of claim 1, further comprising, for each image output from the image repository, automatically executing the stored updated executable code.

16. The method of claim 1, further comprising automatically executing the stored updated executable code as part of performing a search query on the image repository.

17. The method of claim 1, further comprising receiving a selection through the graphical user interface to simulate the executable code and automatically executing the executable code against sample images.

18. The method of claim 1, further including assigning a priority to the executable code based on user input.

19. A system for processing images to unify image data attributes of the images stored in an image repository using user-configurable morphers, the system comprising:
at least one processor configured to;
generate a graphical user interface for display to a user,
receive a matching condition from the user through the graphical user interface,
receive a morphing action from the user through the graphical user interface, the morphing action including an action to perform on a data attribute associated with image data when the image data satisfies the matching condition,
automatically create executable code based on the morphing action and the matching condition and store the executable code,
for each new image received for storage in the image repository,
automatically execute the stored executable code to compare the new image to the matching condition, and
when the new image satisfies the matching condition, automatically perform the morphing action on the new image to generate a morphed version of the new image and store the morphed version of the new image to the image repository,
receive an update through the graphical user interface, the update including at least one of an updated matching condition and an updated morphing action,
automatically create updated executable code based on the update and store the updated executable code, and
for each new image received for storage in the image repository after receiving the update, automatically execute the stored updated executable code.

20. Non-transitory computer-readable medium containing executable instructions for:
generating a graphical user interface for display to a user;
receiving a matching condition from the user through the graphical user interface;
receiving a morphing action from the user through the graphical user interface, the morphing action including an action to perform on a data attribute associated with image data when the image data satisfies the matching condition;
automatically creating executable code based on the morphing action and the matching condition and storing the executable code;
for each new image received for storage in the image repository,
automatically execute the stored executable code to compare the new image to the matching condition, and
when the new image satisfies the matching condition, automatically perform the morphing action on the new image to generate a morphed version of the new image and store the morphed version of the new image to the image repository;
receiving an update through the graphical user interface, the update including at least one of an updated matching condition and an updated morphing action;
automatically creating updated executable code based on the update and storing the updated executable code; and
for each new image received for storage in the image repository after receiving the update, automatically executing the stored updated executable code.

* * * * *